United States Patent [19]

Einbinder

[11] 4,070,699
[45] Jan. 24, 1978

[54] CHARGING CIRCUITS USING CONTROLLED MAGNETIC FIELDS

[75] Inventor: Herbert M. Einbinder, Hackensack, N.J.

[73] Assignee: Datascope Corporation, Paramus, N.J.

[21] Appl. No.: 630,499

[22] Filed: Nov. 10, 1975

[51] Int. Cl.² .................................... H02H 7/122
[52] U.S. Cl. .......................... 361/86; 323/DIG. 1; 363/20; 363/55
[58] Field of Search ............... 317/31, 33 SC, 27 R; 321/2, 11, 14, 18; 323/DIG. 1, 17; 331/112; 361/88, 89, 90, 86

[56] References Cited

U.S. PATENT DOCUMENTS

| | | | |
|---|---|---|---|
| 3,562,623 | 2/1971 | Farnsworth | 321/2 |
| 3,629,686 | 12/1971 | Hetterscheid et al. | 323/DIG. 1 |
| 3,714,545 | 1/1973 | Chiffert | 321/11 X |
| 3,725,739 | 4/1973 | Griffey | 317/33 SC X |
| 3,764,881 | 10/1973 | Thomas | 323/DIG. 1 |
| 3,790,856 | 2/1974 | Hutchinson | 317/33 SC X |
| 3,790,878 | 2/1974 | Brokaw | 321/2 X |
| 3,851,239 | 11/1974 | Suzuki | 321/11 |
| 3,908,159 | 9/1975 | Griffey | 321/11 |

Primary Examiner—J. D. Miller
Assistant Examiner—Patrick R. Salce
Attorney, Agent, or Firm—Steinberg & Blake

[57] ABSTRACT

A circuit for charging an electrical storage device, such as a capacitor, from a source of energy via an induction coil interconnected between the source of energy and the storage device. Current from the source of energy builds up a magnetic field within a primary winding of the coil. A sensing circuit detects a desired maximum value of the magnetic field and then operates a switch to disconnect the primary winding from the source of energy. As the magnetic field starts to collapse, a voltage induced in a secondary winding of the coil enables energy stored in the magnetic field to be transferred to the storage device. When a given minimum value of the collapsing magnetic field is then reached, the primary of the induction coil is reconnected to the source of energy to repeat the above cycle. The minimum of the magnetic field is relatively close to the desired maximum, to permit only a partial magnetic field drop before commencing the next cycle. Protection circuits are included to prevent overcharge of the storage device as well as to terminate the charging process when a predetermined amount of charge has been reached.

5 Claims, 5 Drawing Figures

INDUCTION COIL MAGNETIC FIELD

INDUCTION COIL SECONDARY CURRENT

INDUCTION COIL PRIMARY CURRENT

4,070,699

CHARGING CIRCUITS USING CONTROLLED MAGNETIC FIELDS

BACKGROUND OF THE INVENTION

This invention relates to inverter circuits and more particularly to a circuit for controlling the charge across a capacitor according to the decay of a magnetic field.

There are many systems in the prior art which serve to increase a given potential at an output terminal.

In general, such systems or circuits have been referred to as inverter or converter circuits. Such systems develop a relatively high voltage from a lower voltage source, such as a battery.

The techniques for producing such high voltage outputs have been used in the field of power supplies, photographic flash bulb circuits, pulse laser circuitry, spot welding, and so on.

Essentially, there are many techniques for providing a large voltage from a smaller voltage such as that of a battery.

A number of prior art circuits can be found in a reference entitled "Guidebook for Electronic Circuits" by John Markus, published in 1974 by McGraw Hill, Inc., Chapter 52 entitled "Inverter Circuits". An important application of such circuits is in connection with a portable defibrillator. Such devices are used to provide an electrical pulse of large magnitude for terminating cardiac ventricular fibrillation. In such equipment, the magnitude of the output voltage may be several kilovolts. These devices are portable and battery operated, so that according to the prior art an inverter circuit is used to convert a battery voltage to the required kilovolt level.

A typical circuit used in the prior art includes an oscillator which, powered by the battery, serves to convert the low DC level to an AC signal. The oscillator circuits used typically may comprise a so-called blocking oscillator, astable multivibrator, or some other well known oscillating circuit.

The AC signal output of the oscillator is then applied to a step-up transformer. The turns ratio of this transformer provides an AC signal of considerable voltage at its secondary winding, upon application of the output of the oscillator to the primary winding. The high voltage AC signal at the secondary winding is then conventionally rectified to achieve a DC voltage of large magnitude across a capacitor.

In such circuits, the voltage of the battery is selected to be at least approximately equal to the voltage stored across the capacitor divided by the turns ratio of the transformer.

In order to realize proper operation, a typical prior art circuit of the above type will usually include an impedance to limit the current drawn. This impedance causes a reduction in the charge rate of the capacitor as the voltage across the capacitor increases.

Another disadvantage of such circuits resides in the requirement of a considerable change in battery current due to the charge interval of the capacitor. This factor adversely affects battery life and prevents optimum battery utilizaton.

Also, the size of available batteries necessitates a fairly high transformer turns ratio. Circuit efficiency drops with an increasing turns ration, due to the power loss across the secondary winding of the transformer, so that this factor also is a drawback of the prior art.

Generally speaking, such prior art circuits place stringent requirements on the battery and do not operate reliably as the battery voltage varies or decreases.

Such circuits are not well suited for use in devices such as defibrillators due to the fact that any additional impedance reduces the capacitor charging rate and limits the charging time of the capacitor. Speed of operation is an important aspect of such a device, since the life of a patient is at stake.

Another disadvantage of the prior art resides in the fact that many such circuits require center-tapped transformers, since the circuits exhibit push-pull operation.

Also, most prior art circuits require that the voltage at the secondary winding of the step-up transformer be monitored due to the insertion of the current limiting impedance and due to the fact that current flows simultaneously in both the primary and secondary windings. This monitoring requires high voltage components, due to the high voltage secondary signals.

SUMMARY OF THE INVENTION

Accordingly, it is an object of the present invention to provide a charging circuit which avoids the aforementioned problems of prior art devices.

Specifically it is an object of the present invention to provide a charging circuit which can rapidly charge a storage device.

Still another object of the present invention is to provide a charging circuit operation with a relatively constant load on a battery to improve the efficiency of operation.

A further object of the present invention is to provide a charging circuit which can utilize sources of energy such as batteries having a relatively large range of voltages.

Still another object of the present invention is to provide a charging circuit which can operate without a current limiting impedance and can thus reduce the required time to charge a storage capacitor.

An additional object of the present invention is to provide a charging circuit using a relatively low turns ratio transformer to improve efficiency by reducing power loss.

Yet another object of the present invention is to determine when the storage device has achieved the desired charge by way of a comparator circuit which can compare a reference voltage with the voltage on the primary side of an induction coil.

A further object of the present invention is to provide a charging circuit which avoids simultaneous flow of both primary and secondary current.

As will be explained, the circuit described herein circumvents many of the disadvantages associated with the prior art circuits, while further possessing certain advantages not found in the prior art. Thus, it is among the objects of the invention to achieve advantages which the prior art cannot attain.

While, as indicated, use for a circuit of the above type is in a defibrillator, it is of course, anticipated that the circuit to be described will have uses in other fields which require a large magnitude potential to be derived from a lower magnitude source, such as a battery.

According to the invention an induction coil includes a primary winding, which is coupled to a source of potential such as a battery, and a secondary winding, which is coupled to a storage device such as a capacitor. Current from the battery is applied to the primary winding to cause a magnetic field to build in the primary of the induction coil. When a magnetic field of predetermined magnitude has been achieved within the induction coil, the induction coil is disconnected from the battery by means of a controllable switch, so that the magnetic field in the induction coil starts to collapse. The voltage induced across the secondary winding is transferred to the capacitor which thus becomes charged. After only a small partial collapse of the magnetic field, the primary winding is again coupled to the source of potential to build up the magnetic field to the predetermined magnitude. The storage device is charged in a stepwise fashion, since there is only a partial magnetic field drop before starting the next field build-up cycle. This operation keeps the magnetic field strength near its maximum to reduce the charging time of the capacitor, since the rate of energy transfer is proportional to the magnetic field strength. Consequently, the relative magnitude of the battery source voltage has no appreciable effect on the voltage stored across the capacitor, since the battery is only required to supply enough current to obtain the maximum magnetic field. The source voltage influences the time required to complete the charging of the storage device but not the ability to reach the full charge.

DESCRIPTION OF PREFERRED EMBODIMENTS

Figure 1:
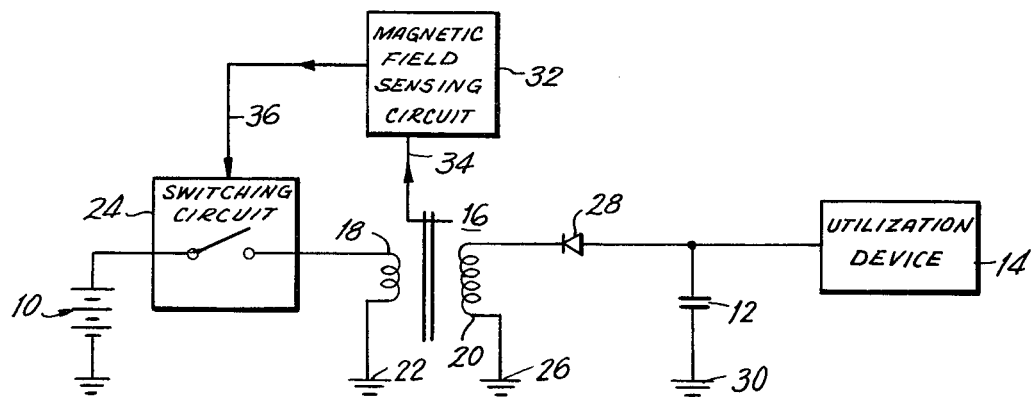
FIG. 1 is a schematic circuit diagram showing the basic features of the present invention.

Referring now to FIG. 1 the circuit therein is schematically shown as including a source of potential or battery 10 for charging an output capacitor 12 which serves as an electrical storage means. When the storage means 12 has been fully charged, the charge therefrom is applied to a utilization device 14. Such a utilization device could be a cardiac defibrillator, a photographic flash lamp, spot and stud welders, an explosive detonating device, etc. A switch (not shown) may be connected in series with the utilization device 14 so that the charge from the storage means 12 will only be sent to the utilization device 14 upon closure of the switch.

Coupled between the battery 10 and the capacitor 12 is an induction coil means 16 having a primary winding 18 and a secondary winding 20. One end of the primary 18 is grounded at 22, and the other end thereof is coupled to the battery 10 through a switching circuit means 24. One end of the secondary 20 is connected to ground at 26, and the other end is connected to the capacitor 12 through a rectifier 28. The other end of the capacitor 12 is connected to ground at 30.

A magnetic field sensing circuit 32 senses the magnetic field within the induction coil 16 along line 34, and provides control through line 36 of the switching circuit 24.

The operation of the circuit shown in FIG. 1 is as follows. When the switching circuit 24 is closed, current flows from the battery 10 through the primary winding 18 to cause a magnetic field to be induced across the induction coil 16. As the field builds up, the current across the primary increases while no current flows in the secondary. When a predetermined maximum magnetic field is reached, the magnetic field sensing circuit 32 senses this maximum field and, in response thereto, controls the switching circuit 24 to disconnect the primary 18 from the battery 10. The magnetic field in the induction coil then starts to collapse. During the field collapse, current flows in the induction coil secondary 20 while no current flows in the primary 18. The decrease in the magnetic field occurs at an accelerating rate during which time the secondary voltage changes in direct proportion to the rate of the field decrease. When the secondary voltage reaches the capacitor voltage, the rectifier 28 conducts and transfers energy stored in the magnetic field of the induction coil to the capacitor, to charge the capacitor and increase its voltage.

After the magnetic field has dropped a predetermined amount to a predetermined minimum field, the magnetic field sensing circuit 32 senses the predetermined minimum field and controls the switching circuit to interconnect the primary 18 again with the battery 10 and start another build-up of magnetic field in the induction coil. The cycle is thus repeated. The cycles of field build-up and field collapse proceed at a continuous rate. During each field build-up, energy is transferred from the battery 10 to the induction coil 16. During each field collapse, energy is transferred from the induction coil 16 to the capacitor 12. The voltage across the capacitor 12 therefore increases in a stepwise manner during each field collapse. When the capacitor reaches its predetermined peak voltage, the entire charging circuit can be disconnected and the voltage maintained across the capacitor until it is desired to be applied to the utilizaton device. Such application can be automatic at regular intervals or can be under control of a particular switch. For example, in defibrillators, or with explosive detonating devices, the charge on the capacitor is maintained until such time as the user wants to utilize the device.

Allowing only a partial magnetic field drop before starting the next cycle of field build-up is one of the features of the present invention. This control, permitting only partial field collapse, serves to minimize the capacitor charging time and also provides optimum battery utilization. In order to understand how the use of only a partial magnetic field drop reduces the charging time, it will be assumed that there is an idealized circuit with stray resistances so small that the battery voltage is constant for all currents and most of the energy drawn from the battery is converted into magnetic field energy in the induction coil. The rate of energy transfer from the battery to the magnetic field is appropriately equal to the power drawn from the battery. This power is also equal to the battery voltage multiplied by the current drawn from the battery. Therefore, assuming a constant battery voltage, the rate of magnetic field energy build-up is proportional to the current. In addition, the magnetic field strength itself is also proportional to the induction coil primary current. Since both the rate of magnetic field energy build-up as well as the magnetic field strength are proportional to the current, it can be concluded that the rate of magnetic field energy build-up is proportional to the magnetic field strength. Thus, the greater the magnetic field strength, the faster the rate of magnetic field energy build-up. When the magnetic field strength is very low, the rate of magnetic field energy build-up will be less than when the magnetic field strength is at a high value. Keeping the magnetic field strength close to its maximum field value, therefore, keeps the rate of magnetic field energy build-up high.

The same result is obtained for the rate of energy transfer from the magnetic field to the capacitor. In this case, the capacitor serves as the equivalent of the battery and the secondary current serves as the equivalent of the primary current. The rate of energy transferred from the secondary to the capacitor will also be proportional to the magnetic field strength. The higher the magnetic field strength, the faster the rate of energy build-up across the capacitor and the greater the rapidity with which the capacitor voltage will reach its peak desired value.

As a result, the most rapid capacitor charging can be obtained by keeping the magnetic field at a relatively high value, thereby allowing only a small amount of field drop during the transfer of energy from the magnetic field to the capacitor. After this small amount of field collapse, the cycle is again started to cause the magnetic field build-up through a relatively small increment to its maximum field value.

Figure 2A:
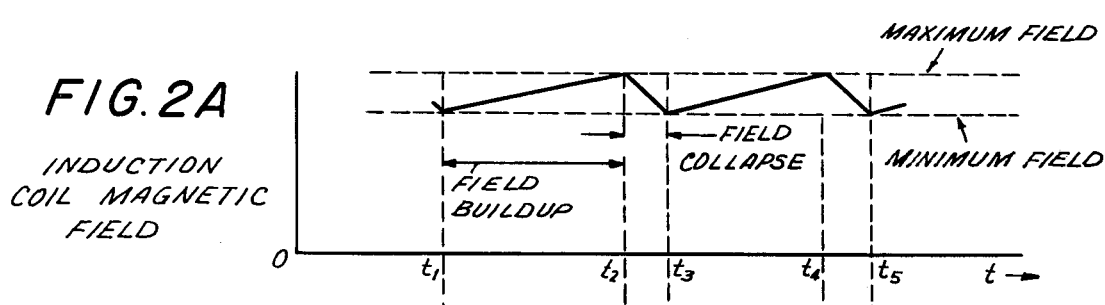
FIG. 2A-2C are graphs illustrating the concepts of the present invention.
Figure 2B:
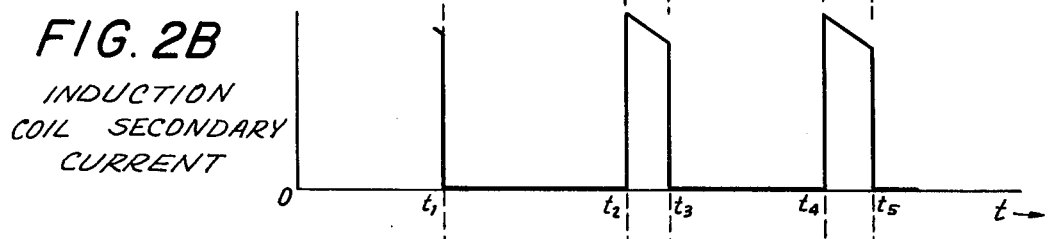
Figure 2C:
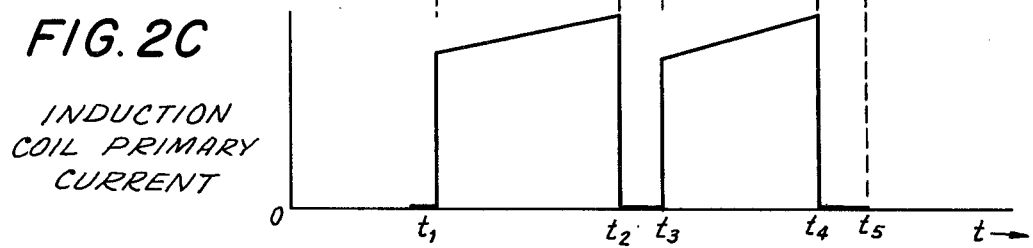

The amount of time saved by permitting only a partial discharge can be better understood by referring to FIGS. 2A–2C, which respectively show graphs of the induction coil magnetic field, the induction coil secondary current, and the induction coil primary current, the graphs all being with respect to time. From time $t1$ to $t2$ the primary is connected to the battery and a magnetic field is built up in the induction coil. During this same time period current flows in the primary at a linearly increasing value whose slope is equal to the battery voltage divided by the induction coil primary inductance. During this time period no current flows in the secondary. When the magnetic field sensing circuit 32 senses a given maximum field across the induction coil at time $t2$, the primary of the induction coil is disconnected from the battery causing an in the drop in the induction coil primary current and increase in the induction coil secondary current. The magnetic field then begins to collapse while the current in the secondary decreases linearly at a rate equal to the capacitor voltage divided by the induction coil secondary inductance. At time $t3$, the predetermined minimum value of magnetic field is sensed and the primary is again connected to the battery to begin field build-up again. Since the magnetic field is proportional to the coil currents, the field build-up and field collapse also change linearly with respect to time. Because of this linear relationship, it is possible to average the field strength over an entire cycle by utilizing well known arithmetic averaging techniques for the maximum and minimum values.

By permitting only a partial magnetic field drop and by keeping the minimum field value high and quite close to the maximum field, the average field between maximum and minimum values is close to the maximum field value itself. If, on the other hand, the magnetic field were allowed to fall to zero during field collapse and subsequently to build-up from zero until the maximum is reached, the average field would be ½ the maximum value. Since the energy transfer rates are proportional to the field strength, permitting only a partial magnetic field collapse as shown in FIG. 2A, provides an energy transfer rate which is quite close to the maximum field value. On the other hand, if the field were allowed to collapse all the way to zero, the energy transfer rate would be ½ the maximum field value. Thus, by way of the present invention only a partial, relatively small field drop is permitted, so that the charging rate is nearly double that obtainable by permitting field collapse to zero. Therefore, the capacitor charging time is nearly half the time required in the case of total field collapse.

Additionally, the partial field collapse provides better utilization of the battery itself. Since the current and the field are proportional to each other, allowing only a small drop in the field also results in only a small change of battery current during the time that the battery is connected to the induction coil primary. Therefore, except for the time when the switching circuit is open and the battery is not connected to the coil, the battery current is nearly constant. The selected ratio of primary coil turns to secondary coil turns enables the switch to be open only a small fraction of the time once some charge has been built up on the capacitor. This feature results in a nearly constant load on the battery and again insures an almost constant battery current. Because essentially constant battery current is utilized, a battery can be chosen to provide a current which is most desirable for the circuit. The battery choice is based upon its size, efficiency, life and reliability.

Figure 3:
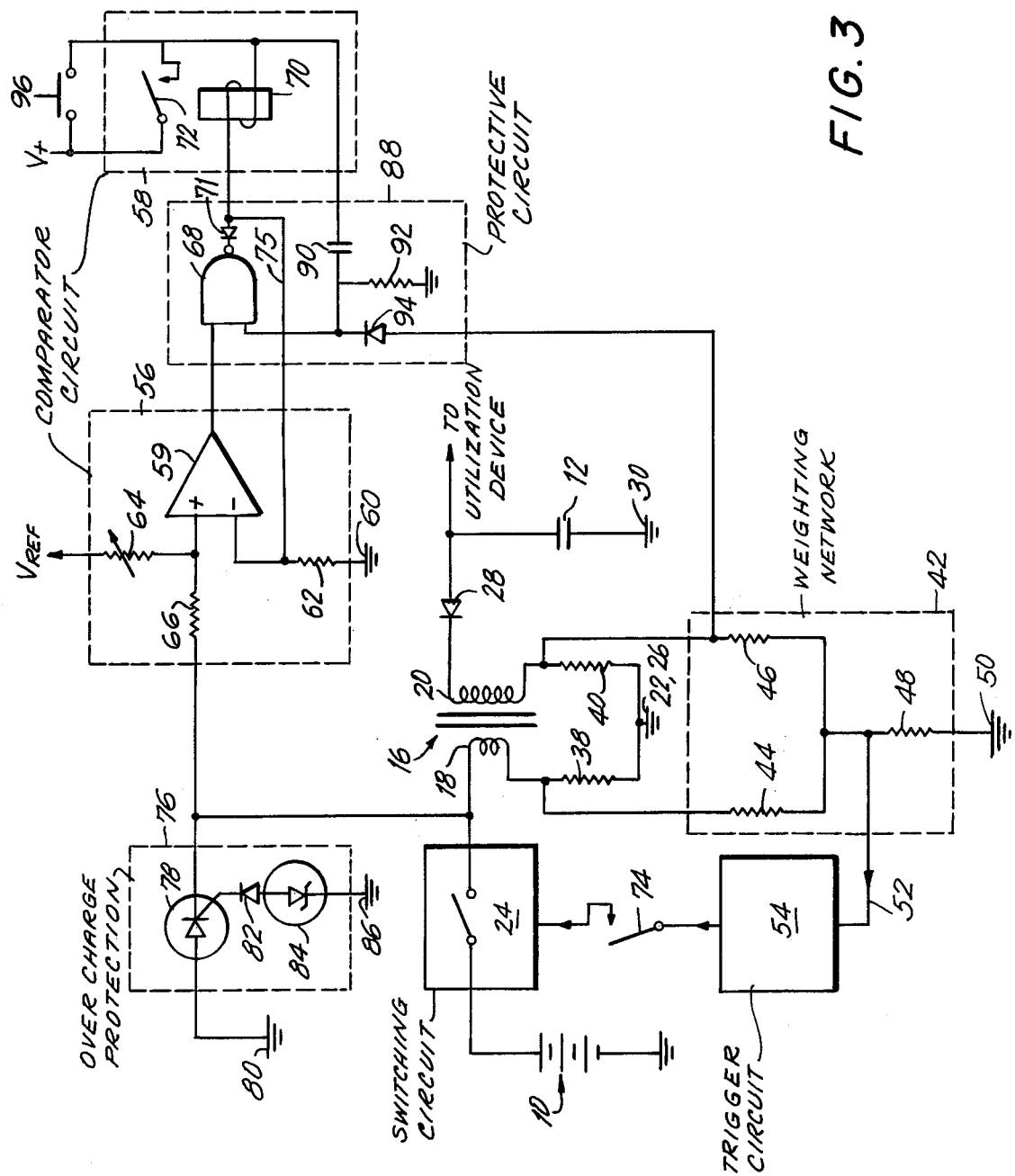
FIG. 3 is a detailed circuit diagram of an embodiment of the present invention, including protection circuits.

Referring now to FIG. 3, there is a more detailed illustration of the charging circuit of the present invention including additional protective circuitry.

In FIG. 3, the magnetic field sensing is accomplished by sensing both the primary and secondary currents by means of shunt resistors 38, 40 respectively placed in series with the primary 18 and the secondary 20 of the induction coil 16. The currents sensed are then added together in a weighting network 42 which includes resistors 44 and 46 respectively connected across shunt resistors 38 and 40. Resistor 48 connects the resistors 44 and 46 to ground 50. The weighting network 42 weights the current in proportion to the primary to secondary turns ratio. Since the magnetic field is directly proportional to the current in the primary and the secondary, by measuring the currents the magnetic field strength can be sensed. The output of the weighting network is received by conductor 52 and delivered thereby to a trigger circuit 54, typically a Schmitt trigger, which controls the switching circuit 24. The Schmitt trigger 54 can be set to have its two trigger values equal to the predetermining maximum and minimum field values. Thus, when the weighting network produces an output determined by maximum field strength, the trigger circuit will open the switching circuit 24. On the other hand, when the weighting network produces an output determined by the minimum field value, the trigger circuit will close the switching circuit 24 and connect the induction coil to the battery 10.

In order to determine when the capacitor has been fully charged to its desired voltage, a comparator circuit is included. The comparator circuit is shown included within dotted lines 56 and 58. The comparator circuit includes a differential amplifier 59 having its negative input coupled to ground 60 through resistor 62. Its positive input is connected to a reference voltage $V_{REF}$ through a variable resistor 64 and at the same time the positive input is connected to the primary 18 of the induction coil 16 through a resistor 66.

The output from the differential amplifier passes through NAND gate 68 to deenergize a relay coil 70 which has two normally open relay switches 72 and 74. The output of the NAND gate 68 is coupled to the coil 70 via a rectifier 71. The anode of the rectifier is connected to the negative input of the differential amplifier 59 through conductor 75.

The comparator circuit operates as follows. The primary coil voltage is sensed across the primary 18 of the induction coil and compared with the predetermined reference voltage. When a peak primary coil voltage which equals the reference voltage is reached, the differential amplifier 59 produces an output which passes through the NAND gate 68 to thereby deenergize the coil 70. The feedback along line 75 keeps coil 70 deenergized until switches 72 and 74 open. When switch 74 opens, the trigger circuit 54 is completely disconnected from the switching circuit 24 thereby removing control from the switching circuit whereby the switching circuit 24 remains in an open position to disconnect the coil primary 18 from the battery 10. The reference voltage is set by way of resistor 64 in accordance with the selected voltage to be stored across the capacitor 12. Thus, when the capacitor 12 reaches the desired maximum voltage after a number of cycles of stepwise charging, the comparator circuit will disconnect the coil from the battery via the relay 70 and thus terminate charging of the capacitor.

It is to be noted that the comparator circuit does not directly measure the voltage across the capacitor; instead it measures the peak primary coil voltage. This ability of inferring the capacitor voltage from the peak primary voltage is one of the features of the charging circuit of the invention. Since the primary current is zero while energy is transferred to the capacitor, no errors are introduced. In certain prior art charging circuits utilizing an inverter and a transformer, both the primary and the secondary currents flow simultaneously so that the capacitor voltage can only be determined at the secondary. Furthermore, it is noted that there is no current limiting impedance in the circuit of the present invention. As a result the reference voltage can be reduced since it is compared to a voltage at the primary side which is less than the voltage at the secondary side. Also, since lower voltages are compared, the differential amplifier can be of a lower rating and the other components of the comparator circuit can be of a type which operate at a reduced voltage.

It is also to be noted that the peak primary voltage can be several times the battery voltage. It is essentially the battery current which is used to charge the induction coil and create the magnetic field. The magnetic field in turn produces the voltage across the induction coil, and this voltage can be considerably higher than the battery voltage itself. This feature permits a lower secondary to primary turns ratio than has been heretofore achieved using an inverter in conjunction with a transformer. The reduction in the turns ratio also results in lesser winding resistances and lesser capacitances. The efficiency of the charging circuit is therefore improved.

An overcharge protection circuit is also included as shown within the dotted lines 76. This circuit includes a thyristor, such as SCR 78, whose anode is connected to ground at 80 and whose cathode is connected to the primary 18 of the induction coil. The gate of the SCR 78 includes a rectifier 82 in series with a Zener diode 84 whose cathode is connected to ground at 86.

The operation of the overcharge protection circuit 76 is as follows. When the peak primary voltage becomes greater than a predetermined amount, as determined by the Zener diode 84, the SCR 78 will turn on and the primary 18 of the induction coil 16 will become short-circuited to ground, thus reducing the voltage thereacross. The purpose of the overcharge protection circuit is to protect the capacitor 12 from a dangerous overcharge in case the comparator circuit 56, 58 should fail. The overcharge protection circuit will also protect the circuit components should the charging circuit become activated while the capacitor is disconnected from the circuit.

A further protective circuit, shown within the dotted lines 88, serves to stop the operation of the circuit if the transfer of energy to the capacitor should be delayed for longer than the usual cycle time. Such excessive delay could result if the overcharge protection circuit is triggered or if the battery 10 weakens so much that it cannot even provide the current needed to obtain the maximum magnetic field across the induction coil 16. The protective circuit 88 includes a timing circuit comprising a capacitor 90 and a resistor 92. The interconnection between the resistor 92 and the capacitor 90 is connected through the rectifier 94 to the junction between the secondary 20 of the induction coil 16 and the resistor 40. The junction between the resistor 92 and the capacitor 90 is also connected as another input to the NAND gate 68.

The resistor 92 and capacitor 90 provide a predetermined time constant based upon what normal circuit cycle time should be for transferring energy from the magnetic field to the capacitor. As long as this normal cycle time is maintained, the protective circuit 88 will have no effect on the charging circuit. However, should there be an excessive delay resulting, for example, from the opening of the overcharge protection circuit 76 or a weakening of the battery 10, the time before charging the capacitor 12 will exceed the predetermined normal time and the capacitor 90 will now discharge, thereby acting through NAND gate 68 to deenergize the relay coil 70 causing relay switches 72 and 74 to open and thereby disconnect the primary 18 from the battery 10 and open the entire circuit.

An initiating switch 96 is included to interconnect a voltage supply $V_+$ to the circuit to initially energize the relay coil 70 as well as the protective circuit 88. The switch 72 will then close to self-retain the coil 70 in an energized state. Also, the switch 74 will close to interconnect the trigger circuit 54 to the switching circuit 24 permitting control over the switching circuit 24 for intermittently connecting the induction coil to the battery.

A typical circuit as shown in FIG. 3 has been operated with a maximum field of about 1.3 Tesla to a minimum field of about 1 Tesla. It is, of course, understood that the selection of these levels can vary, so that a smaller decay or greater or lesser fields can be utilized. A normally twelve volt battery was used in the circuit, but the battery voltage could be raised from seven to eighteen volts without affecting circuit operation.

While an induction coil is preferable, it is understood that any transformer having an applicable air gap can be utilized since the magnetic energy is for the most part stored in the air-gap, and therefore this energy is available to charge the capacitor.

It is apparent that the relay 70 of FIG. 3 can be replaced by an equivalent semiconductor device such as an SCR or transistor circuit, and the same is true of the relay contacts as 72 and 74.

Thus, the operation of the circuit depends upon the transfer of energy from the magnetic field to the electric field with the transfer of energy optimized by keeping the magnetic field within predetermined limits between the maximum and minimum values, so that the capacitor is charged rapidly and independently of the source or battery potential. In connection with this operation, the magnitude of the magnetic field is sensed by responding to the intensity directly or via the current or voltage levels in the windings of the induction coil.

In summation, an inverter circuit has been disclosed which possesses at least the following advantages:

a. a short capacitor charging time, achieved by controlling the magnetic field build-up and collapse betwee maximum and minimum values;

b. more efficient battery use due to the control of the magnetic field between the maximum and minimum values, with this range being relatively small and thus requiring only a small change in battery current, while maintaining a relatively constant load on the battery;

c. the use of simple and relatively low rated components, since relatively lower voltages on the primary winding can be maintained;

d. the use of a wide range of battery voltages since the current for field build-up determines the charging of the capacitor;

e. the elimination of a current limiting impedance since the charge across the output capacitor is primarily the peak primary voltage multiplied by the turns ratio of the induction coil; and f. the accommodation of economical and relatively low rated protection circuits.

Certain advantages and possible variations in structure will be understood by those skilled in the art upon reading the specification and are encompassed within the claims appended hereto.

I claim:

1. In a charging circuit adapted to include a source of energy and comprising electrical storage means, induction coil means connected to said storage means and adapted to be electrically coupled between said source of energy and said electrical storage means, for building a magnetic field when connected to said source of energy and for transferring energy to said storage means when disconnected from said source of energy to provide a drop in the magnetic field, and switching means connected to said coil means and adapted to be connected between said coil means and energy source for repeatedly interconnecting said coil means with said source of energy in successive cycles during each of which said coil means is first connected to said source of energy to build said magnetic field up to a predetermined maximum and is then disconnected from said source to provide said drop, and said switching means starting each cycle when the magnetic field has dropped to a predetermined minimum well above a zero magnetic field so that during operation of the charging circuit there is at said coil means a continuous substantial magnetic field ranging between said maximum and minimum, said coil means being an induction coil having a primary coupled to said switching means and a secondary coupled to said electrical storage means, said induction coil being capable of having energy stored in said magnetic field induced therein, comparator circuit means coupled to the primary of said induction coil, reference voltage coupled to said comparator circuit means for providing a selected reference voltage, said comparator circuit means comparing the voltage across said primary with said reference voltage and producing an output when said voltages are equal, and control means connected between said comparator circuit means and said switching means for opening the latter to disconnect said primary from said source of energy in response to said output.

2. In a circuit as in claim 1 and wherein said comparator circuit means includes a differential amplifier means having said output, a grounded input and a second input coupled to said primary and to said reference voltage means, gating circuit means coupled to said output of said differential amplifier means for responding thereto to produce a gating output, relay coil means coupled to said gating output for responding thereto, said control means including a relay switch controlled by said relay coil means, and feedback means coupled between said gating output and said grounded input of said differential amplifier means.

3. In a circuit as in claim 2 and further comprising protective circuit means for comparing the time duration of each energy transfer with a predetermined time, said protective circuit means being coupled between said relay coil means and said gating circuit means.

4. In a circuit as in claim 2 and further comprising main switch means connected to said relay coil means for initiating operation of the charging circuit.

5. In a charging circuit adapted to include a source of energy and comprising electrical storage means, induction coil means connected to said storage means and adapted to be electrically coupled between said source of energy and said electrical storage means, for building a magnetic field when connected to said source of energy and for transferring energy to said storage means when disconnected from said source of energy to provide a drop in the magnetic field, and switching means connected to said coil means and adapted to be connected between said coil means and energy source for repeatedly interconnecting said coil means with said source of energy in successive cycles during each of which said coil means is first connected to said source of energy to build said magnetic field up to a predetermined maximum and is then disconnected from said source to provide said drop, and said switching means starting each cycle when the magnetic field has dropped to a predetermined minimum well above a zero magnetic field so that during operation of the charging circuit there is at said coil means a continuous substantial magnetic field ranging between said maximum and minimum, said coil means being an induction coil having a primary coupled to said switching means and a secondary coupled to said electrical storage means, said induction coil being capable of having energy stored in said magnetic field induced therein, protective circuit means coupled across said electrical storage means for comparing the time of each energy transfer with a predetermined time interval and responding to an increase in said predetermined time interval to produce a safety output, and control means connected between said protective circuit means and said switching means for opening the latter to disconnect said primary from said source of energy in response to said safety output.

* * * * *